US008162950B2

(12) United States Patent
Digeser et al.

(10) Patent No.: US 8,162,950 B2
(45) Date of Patent: Apr. 24, 2012

(54) BONE PLATE INSTRUMENT AND METHOD

(75) Inventors: Denis Digeser, Bräunlingen (DE);
Jürgen Rettich, Mühlheim (DE);
Jürgen Kraus, Bahlingen (DE); Von Wieding Holger, Kiel (DE); Ingo Stoltenberg, Probsteierhagen (DE)

(73) Assignee: Stryker Leibinger GmbH & Co. KG (DE)

( * ) Notice: Subject to any disclaimer, the term of this patent is extended or adjusted under 35 U.S.C. 154(b) by 1162 days.

(21) Appl. No.: 12/002,519

(22) Filed: Dec. 17, 2007

(65) Prior Publication Data
US 2009/0157086 A1 Jun. 18, 2009

(51) Int. Cl.
*A61B 17/58* (2006.01)

(52) U.S. Cl. ......................................................... 606/96

(58) Field of Classification Search ................ 606/86 B, 606/96, 281
See application file for complete search history.

(56) References Cited

U.S. PATENT DOCUMENTS

| | | | |
|---|---|---|---|
| 2,494,229 A | 1/1950 | Collison | |
| 2,935,905 A | 5/1960 | Winslow | |
| 5,147,367 A | 9/1992 | Ellis | |
| 5,507,801 A | 4/1996 | Gisin et al. | |
| 5,851,207 A | 12/1998 | Cesarone | |
| 5,993,449 A | 11/1999 | Schlapfer et al. | |
| 6,342,057 B1 | 1/2002 | Brace et al. | |
| 6,358,250 B1 | 3/2002 | Orbay | |
| 6,364,882 B1 | 4/2002 | Orbay | |
| 6,379,364 B1 | 4/2002 | Brace et al. | |
| 6,692,503 B2 | 2/2004 | Foley et al. | |
| 6,706,046 B2 | 3/2004 | Orbay et al. | |
| RE38,684 E | 1/2005 | Cesarone | |
| 6,866,665 B2 | 3/2005 | Orbay | |
| 6,926,720 B2 | 8/2005 | Castaneda | |
| 7,081,119 B2 * | 7/2006 | Stihl | 606/96 |
| 7,153,309 B2 | 12/2006 | Huebner et al. | |
| 7,250,053 B2 | 7/2007 | Orbay | |
| 7,282,053 B2 | 10/2007 | Orbay | |

(Continued)

FOREIGN PATENT DOCUMENTS
EP 0 993 275 4/2000
(Continued)

OTHER PUBLICATIONS
Partial European Search Report, EP 07 02 4429.

*Primary Examiner* — Nicholas Woodall
(74) *Attorney, Agent, or Firm* — Lerner, David, Littenberg, Krumholz & Mentlik, LLP

(57) ABSTRACT

A drill guide for a bone plate which has holes therethrough for receiving bone screws. The drill guide includes a guide block having drill guide bores alignable with at least two bone screw receiving holes in the bone plate. A first locking element in inserted through a guide block drill guide bore. The locking element has a tip for engaging a bone screw receiving holes in the bone plate, the tip being selectively expandable to engage and disengage from the bone plate hole. A second locking element is mounted on the guide block and is engageable with a bone plate hole. The second locking element also has a tip for resiliently engaging walls of the bone plate hole wherein the tip of the first and second locking elements has a split portion. The first and second locking elements include an axially moveable rod for expanding the split tip portion to engage the plate 11 Claims, 8 Drawing Sheets

U.S. PATENT DOCUMENTS

| | | |
|---|---|---|
| 7,294,130 B2 | 11/2007 | Orbay |
| 2003/0040748 A1 | 2/2003 | Aikins et al. |
| 2005/0085818 A1* | 4/2005 | Huebner .................. 606/69 |
| 2005/0137606 A1* | 6/2005 | Binder et al. ............. 606/96 |
| 2006/0095044 A1 | 5/2006 | Grady et al. |
| 2006/0100637 A1 | 5/2006 | Rathbun et al. |
| 2006/0173458 A1 | 8/2006 | Forstein et al. |
| 2007/0191855 A1 | 8/2007 | Orbay et al. |

FOREIGN PATENT DOCUMENTS

| | | | |
|---|---|---|---|
| JP | 2009178543 A | * | 8/2009 |
| WO | 01/82804 | | 11/2001 |
| WO | 2006081483 | | 8/2006 |

* cited by examiner

BONE PLATE INSTRUMENT AND METHOD

BACKGROUND OF THE INVENTION

The present invention relates to a bone plating system and instrumentation used in the fixation of fractures of long bones such as the femur, tibia, humerus and radius, including peri-articular fractures. More specifically, the present invention encompasses a bone plating system that aids in the location of bone screws and drilling of pilot holes for the placement and intraoperative adjustment and fixation of the plate to the fractured bone.

Typical fixation of a fracture of a long bone with a bone plate requires making an incision in the tissue, reducing the fracture, placing a bone plate on the fractured bone, and securing the bone plate to the bone with fixation elements such as screws. The bone plate immobilizes the fracture and keeps the bone in a correct position so as to allow the fracture to heal.

Typically, bone plates have a bone contacting side and a side facing away from the bone with a plurality of holes or apertures extending between the two surfaces. These holes or apertures may be either threaded (for use with locking screws) or non-threaded (for use with regular screws) and may be circular or oblong in shape.

In order to allow for a reliable stabilization of a broken bone in its normal position, special bone stabilizing implants are frequently used. Such implants are for instance metal plates, which are made e.g. from surgical steel. Plates used for such purposes are usually fixed to the bone parts by means of threaded screws, which are driven into the bone tissue after so-called pre-drilled or pilot-drilled holes have been generated in the bone tissue. These pre-drilled holes allow for a reliable screwing procedure whereby the risk of further destroying the bone with the screw is significantly reduced.

In order to facilitate the drilling of these pre-drilled holes there are known so-called aiming or targeting devices, which work like a drilling jig. Thereby, an aiming or targeting device is detachably fixed to the metal plate in a precise position.

One such bone plate is shown in U.S. Pat. No. 6,623,486 in which the plate has a head portion for placement adjacent the metaphysis of the bone and a shaft portion for placement against the diaphysis of the bone. The plate includes both locking (threaded) holes and non-locking holes. The locking holes are adapted to receive bone screws with threaded heads or proximal areas which engage the threads in the locking holes to thereby lock the screw to the plate. Bone screws without threaded heads can be then inserted into the non-locking holes or into the oblong holes which oblong holes permit the screws to be oriented at various angles.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

Various aspects of the present invention are achieved by a drill guide for a bone plate having holes therethrough for receiving bone screws which guide includes a guide block having drill guide bores alignable with at least two bone screw receiving holes in the bone plate. A first locking element extends through a guide block drill guide bore. The first locking element has a tip for engaging a bone screw receiving holes in the bone plate. The tip is selectively expandable to engage and disengage from the bone plate hole. A second locking element is mounted on the guide block and is engageable with a bone plate hole. The second locking element has a tip for resiliently engaging walls of the bone plate hole. The tip of the first locking element has a split portion and the first locking element includes an axially moveable rod for expanding the split tip portion.

The first locking element includes a threaded axial bore for receiving the axially moveable rod and wherein the axially moveable rod is threaded whereby rotation of the threaded rod moves the rod into and out of engagement with the split tip portion of the first locking element. The split tip has at least two branches formed by axially extending slots open at a free end of the first locking element tip. The first locking element includes an antirotation pin extending radially of a guide bore axis for engaging an anti-rotation feature of the guide block in the form of radially extending open grooves.

The second locking element has a central bore and a tip split into at least two branches surrounding the bore wherein the tip has four branches separated by slots open to a free end of the tip. Preferably, the branches have a lip formed adjacent the free end for engaging a reduced diameter area in the bone plate bore wherein the lip has a smaller diameter than a portion of the second locking element extending through the guide block hole.

A method for drilling holes in bone for receiving bone screws includes placing a bone plate having at least two bone screw receiving holes therethrough on a bone. A drill guide block is then placed on the bone plate, the drill guide block has at least two drill guide bores and is placed in alignment with the bone screw receiving holes of the bone plate. The first locking element is inserted into a first of the drill guide bores of the guide block and into engagement with a corresponding first bone screw receiving hole in the bone plate. A second locking element mounted on the drill guide block is inserted into engagement with a hole in the bone plate. A hole is drilled in the bone using a second drill guide bore on the drill guide block and through a second bone screw receiving hole on the bone plate.

DETAILED DESCRIPTION

Figure 1:
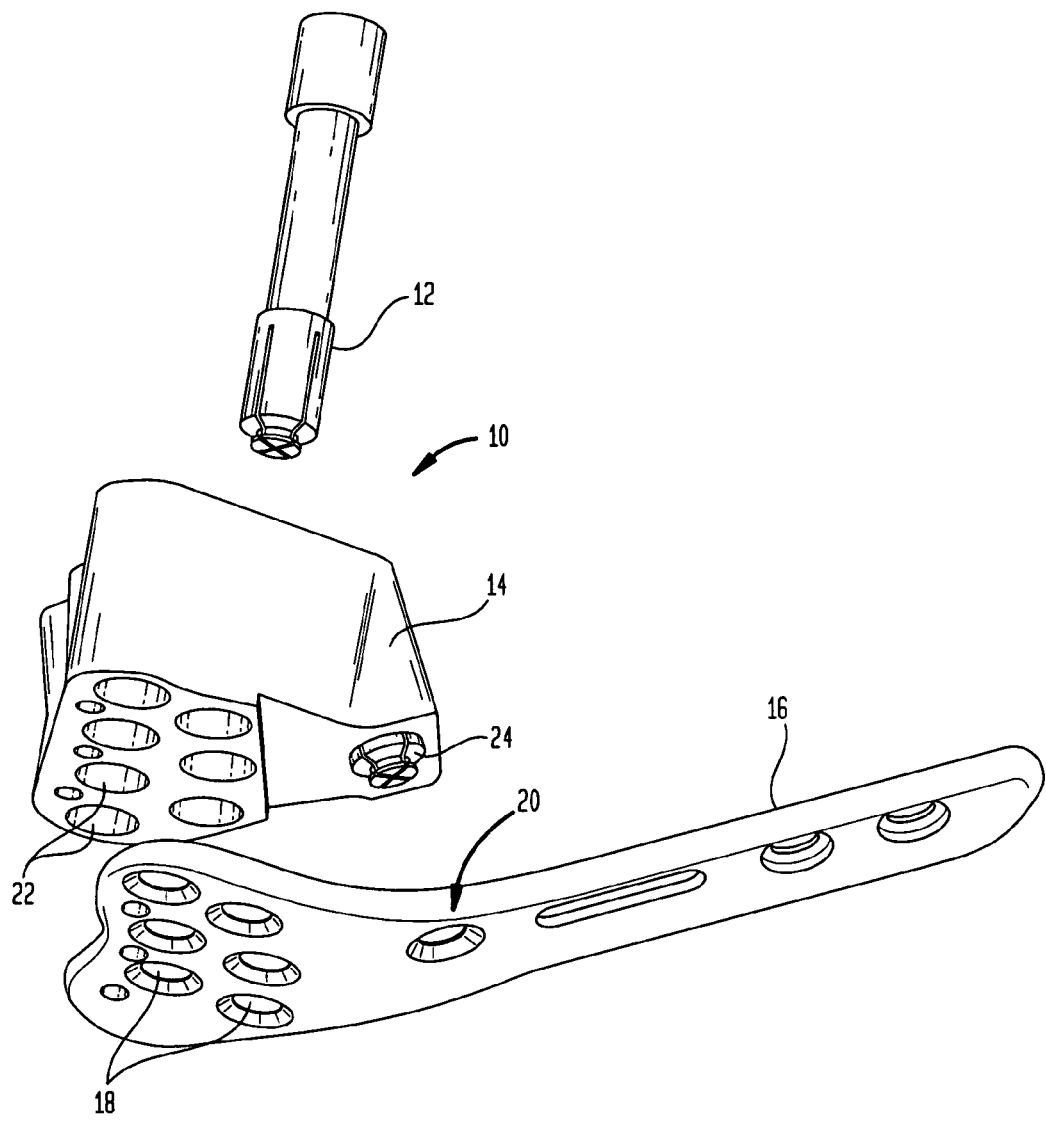
FIG. 1 is an exploded view of the bone plate instrumentation of the present invention including a bone plate, drill guide aiming block and a first locking element adapted to lock the drill guide block to the bone plate.

Referring to FIG. 1 there is shown an exploded view of the instrumentation of the present invention generally denoted as 10. Instrumentation 10 includes a first locking element in the form of a spreading pin 12 and a drill guide block 14. Also shown is a bone plate 16 including a plurality of holes 18 at one end thereof. The bone plate 16 may be angled to match the bone anatomy. The bone plate 14 also includes a hole 20 spaced intermediate the bone plate along a longitudinal axis thereof. All of the bone plate holes may have an internal circumferential area of reduced diameter formed from a circumferential radially inwardly extending rib having a wedge shape. Guide block 14 includes a plurality of holes 22 which are alignable with the holes 18 of the bone plate and are adapted to receive a drill guide so that pilot holes may be drilled in the bone on which bone plate 16 is to be mounted. Also shown mounted in guide block 14 is a second locking element 24 which is insertable into hole 20 of bone plate 16.

Figure 2:
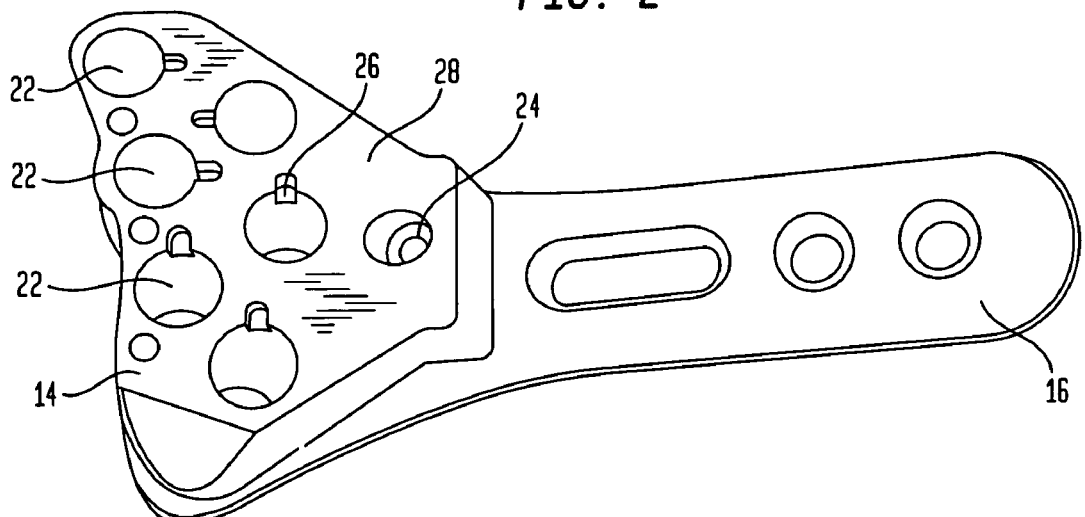
FIG. 2 is a view of the bone plate and guide block of FIG. 1 partially assembled using a second locking element.

Referring to FIG. 2 there is shown guide block 14 mounted on bone plate 16 utilizing the second locking element 24. Also shown in FIG. 2 is an anti-rotation groove or recess 26 which is formed in the outwardly facing surface 28 of guide block 14. The function of this recess 26 will be described in greater detail below.

Figure 3:
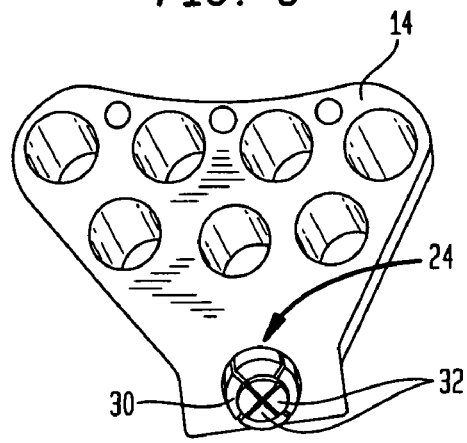
FIG. 3 is a bottom view of the guide block of FIG. 2 showing the second locking element extending partially out of the guide block.

Referring to FIG. 3 there is shown a bottom view of guide block 14 disassembled from bone plate 16 showing the split expandable tip configuration 30 of second locking element 24. As can be seen the preferred split tip 30 includes four branches 32 which can radially expand to engage the walls forming hole 20 of bone plate 16. In the preferred embodiment the expanding branches deform outwardly in a resilient fashion and engage the rib around the walls of the bone plate holes.

Figure 4:
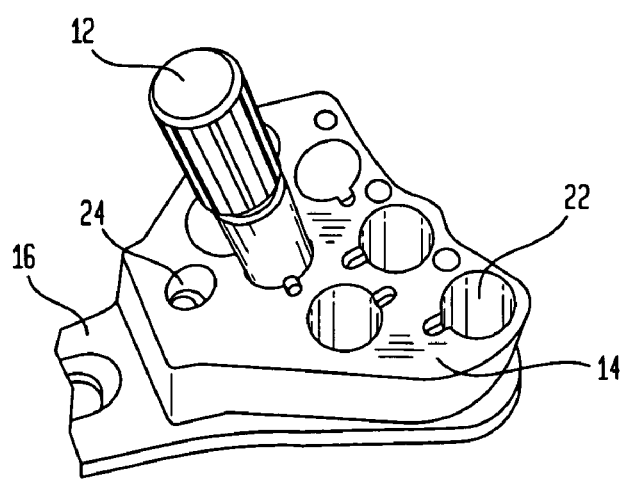
FIG. 4 is a fully assembled view of the first locking element guide block second locking element and bone plate rigidly coupled together.
Figure 5:
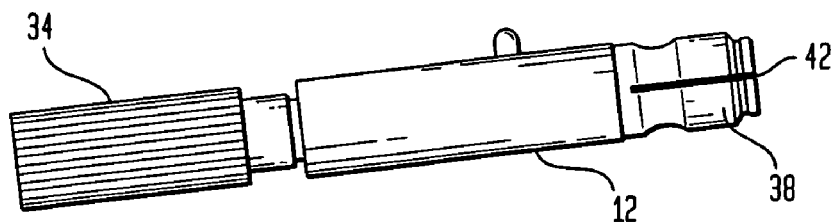
FIG. 5 is an isometric view of the first locking element.

Referring to FIG. 4 there is shown the guide block 14 coupled to bone plate 16 with both the first and second locking elements 12 and 24 respectively. First locking element 12 is designed to be received within any of the guide bores 22 of drill guide block 14 which guide bores are aligned with the holes 18 of bone plate 16. Locking elements 12 and 24 have expanding tips for engaging the bone plate 16.

Figure 6:
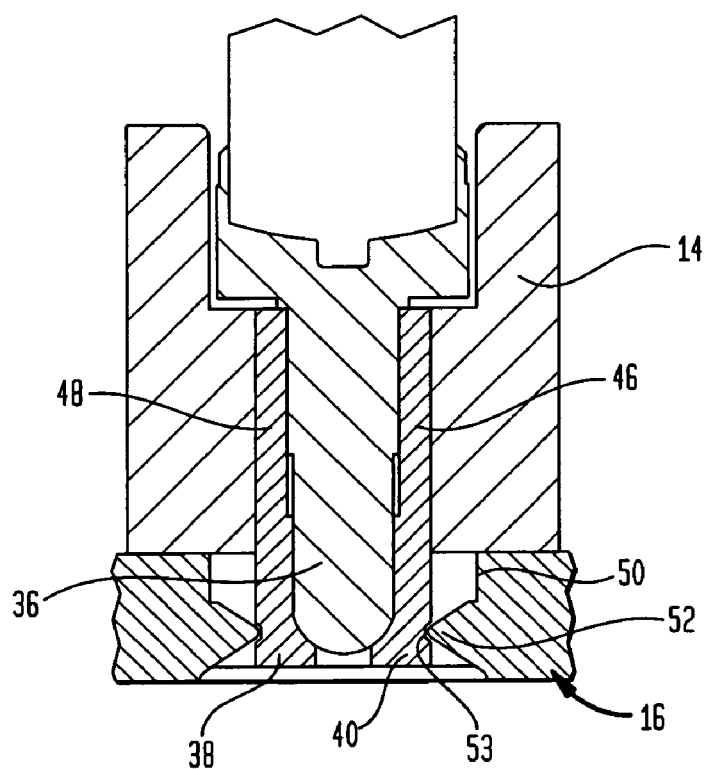
FIG. 6 is an exploded cross-sectional view of the tip of the first or second locking element extending through the guide block and engaging in the bone plate.
Figure 7:
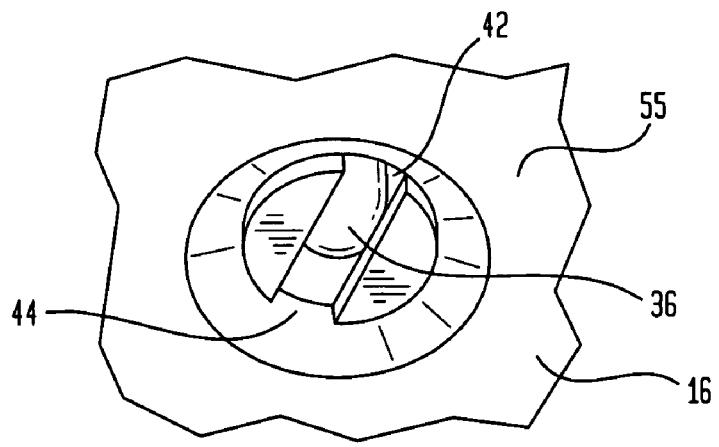
FIG. 7 is an isometric bottom view of the bone plate including the locking element and axially moveable spreading pin of the present invention.

Referring to FIGS. 5-9 there is shown details of the first locking element 12. This includes a handle or rotatable knob portion 34 which rotates a threaded actuating rod 36 in a threaded bore best shown in FIG. 6 which moves rod 36 axially within an expandable tip 38 of first locking element 12. The expandable tip 30 can be bifurcated as shown in FIG. 7 or may contain three, four or even more branches. The branches are separated by slits or slots extending from an open end 40 of expandable tip 38 towards rotating element 34. In the embodiment shown in FIGS. 6 and 7 there are two slits or slots 42 and 44 which form two tip branches 46 and 48. The slits or slots allow the branches to deform outwardly in a resilient fashion such that when the actuating rod 36 is removed the branches spring inwardly.

Figure 8:
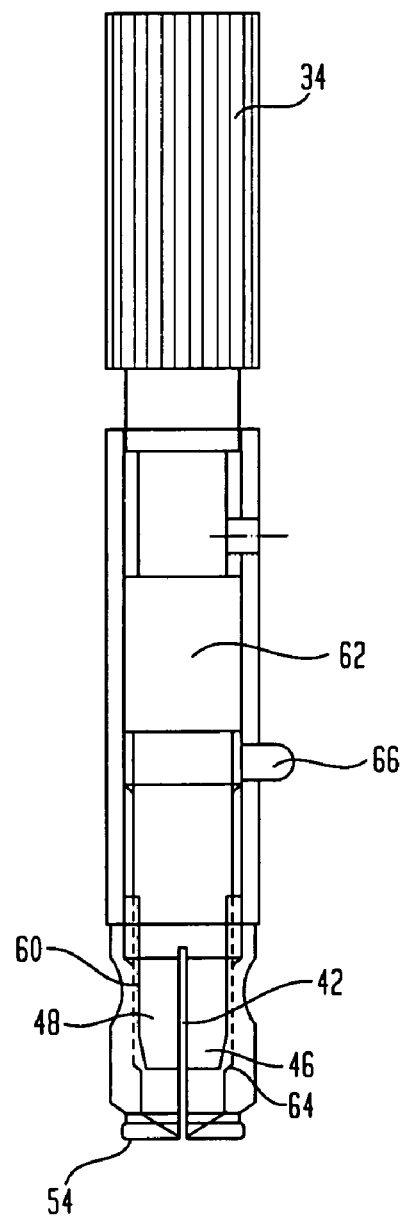
FIG. 8 is an elevation view of the first locking element of the present invention.
Figure 8A:
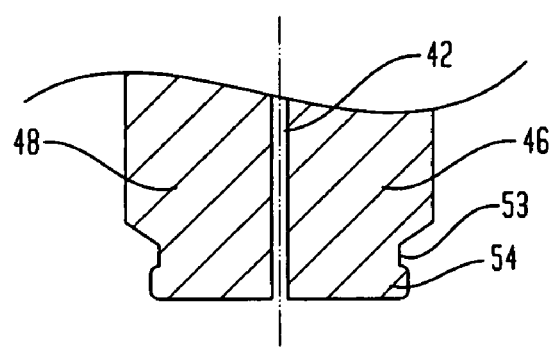
FIG. 8A is a view of the tip of the locking element of FIG. 8.
Figure 9:
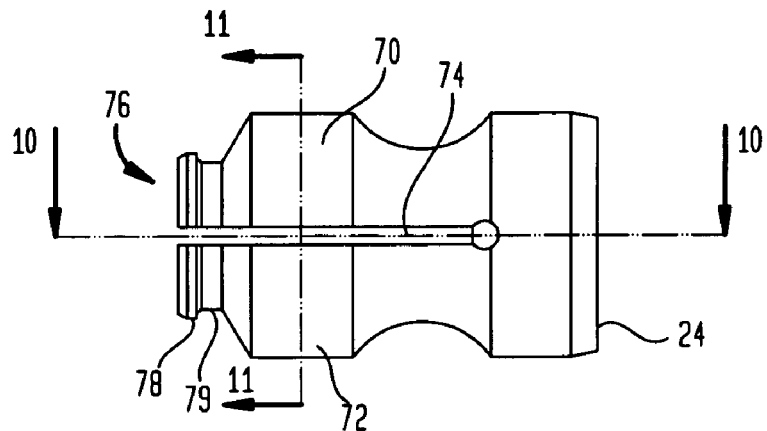
FIG. 9 is an elevation view of the second locking element of the present invention.

As best shown in FIG. 6 bone plate 16 includes bores or holes 18 each having an inner wall 50 including a radially inwardly extending circumferential rib 52. In the preferred embodiment as shown in FIG. 7 the bone contacting surface 55 of the bone plate 16 surrounding hole 18 is recessed such that the rib 52 is located intermediate the outer bone plate surface and the bone contacting bone plate surface 55. As best seen in FIG. 8a the end 38 of the first locking element 12 includes a lip 54 defining a recess 53 for receiving circumferential rib 52 of bone plate hole 18 inner wall 50. The inner bore 60 of the tip 38 of first locking element 12 is threaded to receive a threaded outer surface on pin 36. Pin 36 is coupled to a rotatable drive shaft 62 which can be rotated by turning knob or handle 34. Rotation of knob or handle 34 rotates rod 36 moving into and out of engagement with an inner shoulder 64 of end 38 which causes the branches 46 and 48 to expand outwardly such that lip 54 locks the first locking element to bone plate 16. The first locking element 12 includes a radially outwardly extending pin 66 which is located to engage recess 26 which extends radially outwardly of a central axis of each bore 22 in the outer surface 28 of guide block 14. This prevents rotation of the tip 30 within bores 22 as knob or handle 34 is rotated to expand tip 30.

Figure 10:
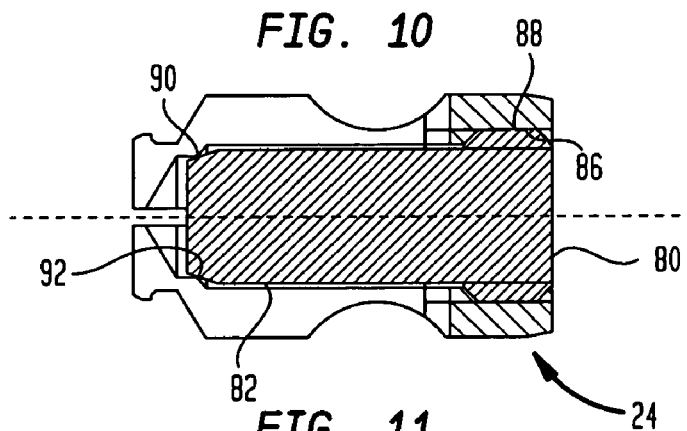
FIG. 10 is a cross-sectional view of the second locking element of FIG. 9 along lines 10-10.
Figure 11:
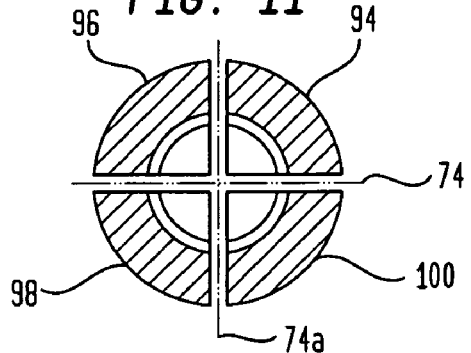
FIG. 11 is a cross-sectional view of the second locking element along lines 11-11 of FIG. 9.
Figure 12:
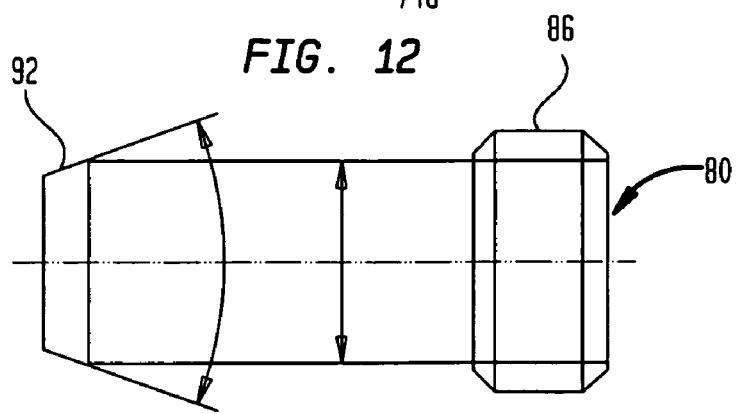
FIG. 12 is an elevation view of a spreading pin as shown in FIG. 10.

Second locking element 24 is shown in FIGS. 9-12 and may be similar in structure to tip 30 of first locking element 12 in that it includes at least two branches 70 and 72 separated by a pair of slots 74. The leading end 76 of second locking element 24 includes a lip 78 identical to lip 54 of first locking element 12 and a recess 79 adapted to receive rib 52. As shown in FIGS. 10 and 12 a threaded spreading rod 80 is insertable into a bore 82 of second locking element 24 and may be threaded inwardly into locking element 24 by engagement of threads 86 on locking pin 80 and threads 88 on an inner bore of the second locking element 24. Locking element 24 includes a shoulder 90 which extends circumferentially around inner bore 82 and engages a bevel 92 of drive screw 80. As can be seen in FIG. 11 in a preferred embodiment the end 76 of second locking element 24 consists of four branches 94, 96, 98 and 100 separated by slots 74 and 74a.

Alternately the branches 94, 96, 98 and 100 of the second locking element may be deformed outwardly during the manufacturing process so that they resiliently deflect inwardly when inserted into the hole in the bone plate. This occurs as beveled end 92 engages the wedge-shaped rib 52 of the bone plate hole 18. Upon further axial insertion the branches snap outwardly and with recess 77 receiving the rib 52. Thus in this embodiment the need for rod 80 is eliminated.

Figure 13:
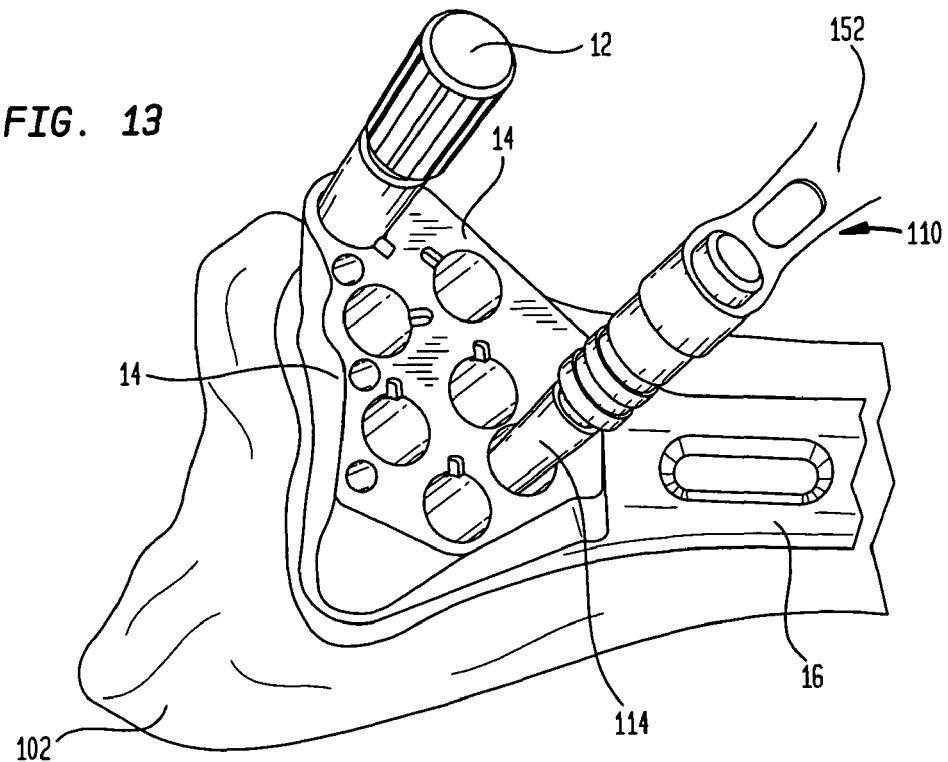
FIG. 13 shows the step of placing a drill guide in the guide block of the present invention.
Figure 14:
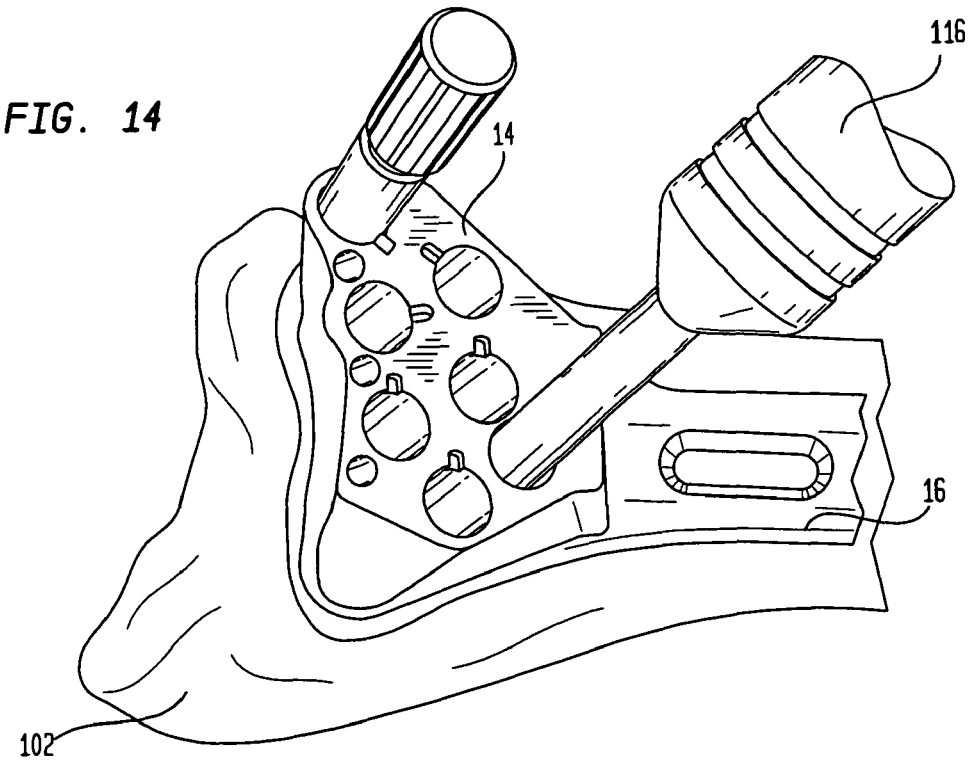
FIG. 14 shows the step of measuring the depth of the hole drilled with the drilling guide of FIG. 13.
Figure 15:
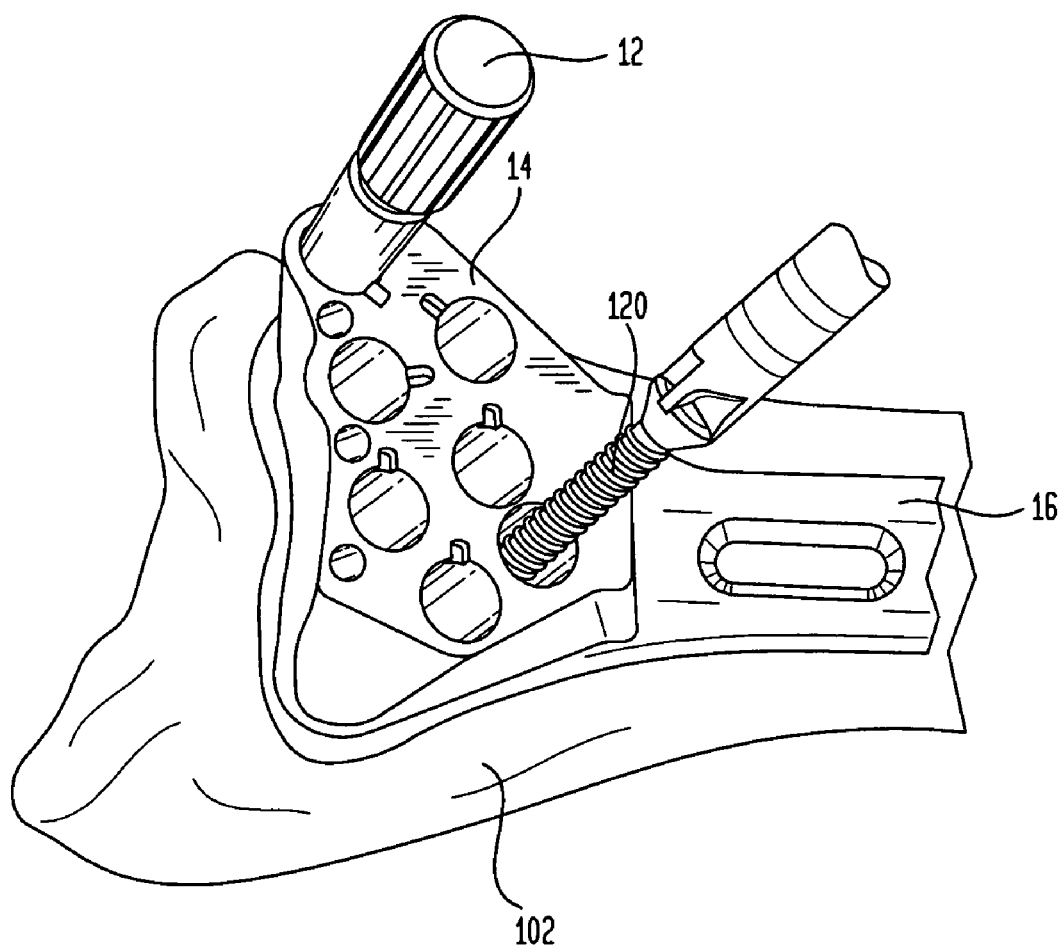
FIG. 15 shows the step of inserting a screw in the hole drilled in bone through the guide block and bone plate.
Figure 16:
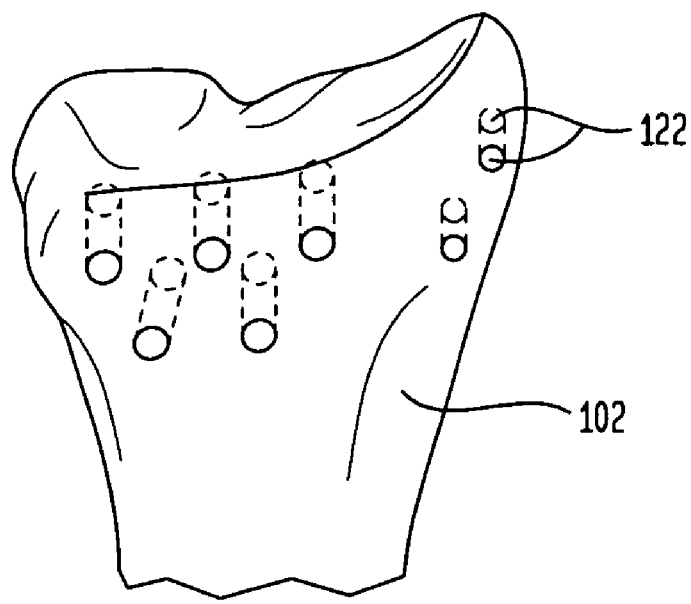
FIG. 16 is an isometric view of a distal radius showing a plurality of pilot holes drilled in the bone for the receipt of bone screws.

Referring to FIGS. 13-15 there is shown the method of forming pilot holes of the present invention. Initially, the bone plate 16 is located on an end of a long bone such as a radius 102 and the block 14 is placed on bone plate 16 with its guide bores 22 aligned with the holes 18 in plate 16. The guide block 14 is held onto the plate by the first and second locking elements 24 respectively with the first locking element extending through one of the guide bores 22. Any convenient guide bore 22 may be chosen. As shown in FIG. 13 a drill guide 110 includes a handle 112 a tubular guide 114 which receives a drill bit (not shown). The drill bit is powered by a pneumatic or electric drill and is adapted to form pilot holes 122 in the bone as shown in FIG. 16. The drill guide is moved from one bore 22 to the next bore 22 and pilot holes are drilled in all the bone plate holes 18. The last pilot hole is drilled in the guide bore which initially had the first locking element 12. Locking element 12 is placed in a guide bore which has been already used to drill a pilot hole and the drill guide is placed in the hole just vacated by the first locking element and that pilot hole is drilled.

Referring to FIG. 14 there is shown a depth gauge 116 of any conventional type and is used to measure the depth of the pilot hole drilled. If that hole is not drilled deeply enough the hole may be re-drilled using the drill guide 110.

Figure 17:
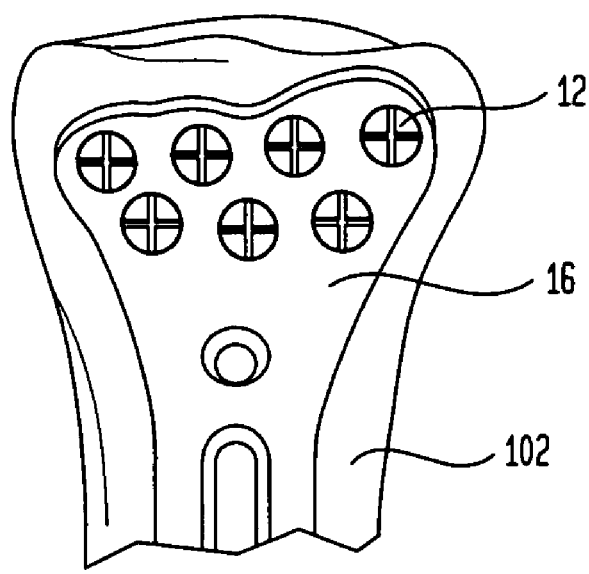
FIG. 17 shows a bone plate assembled to the distal radius as shown in FIG. 16 with bone screws.

Referring to FIG. 15 there is shown the insertion of a typical bone screw 20 into the bone through guide block 14 and into engagement with plate 16. Referring to FIG. 16 there is shown the end of the radius 102 with a plurality of pilot holes 122 drilled therein. Bone plate 16 is placed over these holes with the plate holes 18 aligned therewith when plate 16 is mounted on the bone 102. FIG. 17 shows the plate mounted on bone 102 with the bone screws 120 set in the plate 116 thereby locking the upper end of the plate to the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for drilling holes in bone for receiving bone screws comprising:
   placing a bone plate having at least two bone screw receiving holes therethrough on a bone;
   placing a drill guide block on the bone plate, the drill guide block having at least two drill guide bores placed in alignment with the bone screw receiving holes of the bone plate;
   inserting a first locking element into a first of the drill guide bores of the guide block and into engagement with a corresponding first bone screw receiving hole in the bone plate;
   inserting a second locking element mounted on the drill guide block into engagement with a hole in the bone plate; and
   drilling a hole in the bone using a second drill guide bore on the drill guide block and through a second bone screw receiving hole on the bone plate and further comprising removing the first locking element from the first drill guide bore and inserting the first locking element in the second drill guide bore and drilling a hole in the bone using the first drill guide bore.

2. The method as set forth in claim 1 further comprising selectively expanding a tip of the first locking element engaging the bone plate hole to lock the guide block to the bone plate hole.

3. The method as set forth in claim 2 wherein the tip of the first locking element has a split portion having at least two branches, the first locking element includes an axially moveable rod for expanding the split tip portion by moving the branches outwardly.

4. The method as set forth in claim 3 wherein the first locking element includes a threaded axial bore for receiving the axially moveable rod and wherein the axially moveable rod is threaded whereby rotation of the threaded rod moves the rod into and out of engagement with the split tip portion.

5. The method as set forth in claim 4 wherein the split tip branches are formed by axially extending slots open at a free end of the first locking element tip.

6. A method for drilling a hole in bone for receiving bone screws comprising:
   placing a bone plate having at least three holes therethrough on a bone;
   placing a drill guide block on the bone plate, the drill guide block having at least three drill guide bores therein and aligning the at least three drill guide block bore with the at least three holes in the bone plate;
   inserting a first locking element in a first of the aligned bores and inserting a second locking element in a second aligned bore;
   drilling a hole in the bone through a third bore in the drill guide bore and an aligned third bone plate bore wherein the drill guide block has at least three bores corresponding to at least three holes in the bone plate and has first and second locking elements for extending through the first and second aligned bores in the drill guide block and bone plate and lockingly engaging the bone plate wherein each locking element has a tip with a split portion and includes an axially moveable rod for expanding the split tip portion and wherein the first locking element includes a threaded axial bore for receiving the axially moveable rod and wherein the axially moveable rod is threaded whereby rotating the threaded rod moves the rod into and out of engagement with the split tip portion of the locking element.

7. The method as set forth in claim 6 wherein the split tip has at least two branches formed by axially extending slots open at a free end of the first and second locking element tip.

8. The method as set forth in claim 6 further comprising removing the first locking element from the first bore in the drill guide block and bone plate and inserting the first locking element in a second bore in the drill guide block and bone plate and drilling a hole in the bone through the first bore.

9. A method for drilling holes in bone for receiving bone screws comprising:
   placing a bone plate having at least two bone screw receiving holes therethrough on a bone;
   placing a drill guide block on the bone plate, the drill guide block having at least two drill guide bores placed in alignment with the bone screw receiving holes of the bone plate;
   inserting a first locking element into a first of the drill guide bores of the guide block and into engagement with a corresponding first bone screw receiving hole in the bone plate;
   inserting a second locking element mounted on the drill guide block into engagement with a hole in the bone plate; and
   drilling a hole in the bone using a second drill guide bore on the drill guide block and through a second bone screw receiving hole on the bone plate further comprising selectively expanding a tip of the first locking element engaging the bone plate hole to lock and release the guide block to the bone plate hole wherein the tip of the first locking element has a split portion having at least two branches, the first locking element includes an axially moveable rod for expanding the split tip portion by moving the branches outwardly, wherein the first locking element includes a threaded axial bore for receiving the axially moveable rod and wherein the axially moveable rod is threaded whereby rotation of the threaded rod moves the rod into and out of engagement with the split tip portion.

10. The method as set forth in claim 9 wherein the split tip branches are formed by axially extending slots open at a free end of the first locking element tip.

11. A method for drilling a hole in bone for receiving bone screws comprising:

placing a bone plate having at least three holes therethrough on a bone;

placing a drill guide block on the bone plate, the drill guide block having at least three drill guide bores therein and aligning the at least three drill guide block bore with the at least three holes in the bone plate;

inserting a first locking element in a first of the aligned bores and inserting a second locking element in a second aligned bore;

drilling a hole in the bone through a third bore in the drill guide bore and an aligned third bone plate bore wherein the drill guide block has at least three bores corresponding to at least three holes in the bone plate and has first and second locking elements for extending through the first and the second aligned bores in the drill guide block and bone plate and lockingly engaging the bone plate, removing the first locking element from the first bore in the drill guide block and bone plate and inserting the first locking element in a second bore in the drill guide block and bone plate and drilling a hole in the bone through the first bore.

* * * * *